United States Patent
Bessard et al.

(10) Patent No.: US 6,600,046 B2
(45) Date of Patent: Jul. 29, 2003

(54) PROCESS FOR PREPARING 1-(6-METHYLPYRIDIN-3-YL)-2-[4-(METHYLSULFONY)PHENYL]ETHANONE

(75) Inventors: Yves Bessard, Sierre (CH); James Edward Leresche, Visp (CH)

(73) Assignees: Merck & Co., Inc., Rahway, NJ (US); Lonza AG, Basel (CH)

(*) Notice: Subject to any disclaimer, the term of this patent is extended or adjusted under 35 U.S.C. 154(b) by 0 days.

(21) Appl. No.: 10/283,167

(22) Filed: Oct. 30, 2002

(65) Prior Publication Data

US 2003/0088107 A1 May 8, 2003

Related U.S. Application Data

(62) Division of application No. 10/030,096, filed as application No. PCT/EP00/06825 on Jul. 17, 2000.
(60) Provisional application No. 60/186,680, filed on Mar. 3, 2000.

(30) Foreign Application Priority Data

Jul. 27, 1999 (EP) ................................. 99114667

(51) Int. Cl.[7] ................. C07D 213/46; A61K 31/44
(52) U.S. Cl. ........................ 546/315; 514/355
(58) Field of Search ................ 546/315; 514/355

(56) References Cited

U.S. PATENT DOCUMENTS

| 3,717,647 A | 2/1973 | Villani |
| 4,115,578 A | 9/1978 | Miller et al. |
| 4,118,461 A | 10/1978 | Miller et al. |
| 4,380,544 A | 4/1983 | Dorn |

FOREIGN PATENT DOCUMENTS

| EP | 0062238 | 10/1982 | |
| WO | 98/03484 | 1/1998 | |
| WO | 98/47871 | 10/1998 | |
| WO | WO-9915503 | * 4/1999 | ......... C07D/213/00 |

OTHER PUBLICATIONS

Friesen, R.S., et al., Biorganic & Medical Chemistry Letters, 8, (1998), 2777–2782.
International Search Report for applicants corresponding International Patent Application.
Burger, A., and C.R. Walter, J., of American Chemical Soc., vol. 72, No. 5, (May 1950), pp. 1988–1990.

* cited by examiner

*Primary Examiner*—Alan L. Rotman
*Assistant Examiner*—Janet L Coppins
(74) *Attorney, Agent, or Firm*—Fisher, Christen & Sabol

(57) ABSTRACT

The process for preparing 1-(6-methylpyridin-3-yl)-2-[(4-methlsulfonyl)-phenyl]ethanone of the formula I:

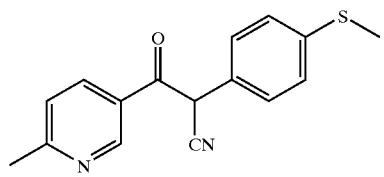

In a first step, 4-(methylthio)phenylacetonitrile is condensed with a 6-methylnicotinic ester to give 3-[2-(4-(methlthio)phenyl)-2-cyanoacetyl](6-methyl)pyridine of the formula II:

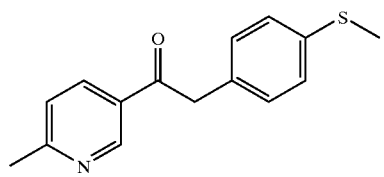

In a second step, the compound of formula II is hydrolyzed and decarboxylated under acidic conditions using a mixture of acetic acid and a mineral acid, to give 3-[2-(4-(methylthio)phenyl)acetyl](6-methyl)pyridine of the formula III:

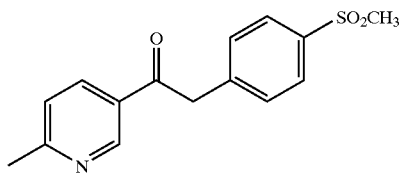

Finally, in a last step, the compound of formula III is oxidized to give the end product.

2 Claims, No Drawings

PROCESS FOR PREPARING 1-(6-METHYLPYRIDIN-3-YL)-2-[4-(METHYLSULFONY)PHENYL]ETHANONE

This is a division of U.S. application Ser. No. 10/030, 096, filed on Mar. 14, 2002, that is a 371 of PCT/EP00/06825, filed on Jul. 17, 2000, that has priority benefit of European Patent Application 99114667.1, filed on Jul. 27, 1999, and of U.S. Provisional Application No. 60/186,680, filed on Mar. 3, 2000.

The invention encompasses a novel process for preparing 1-(6-methylpyridin-3-yl)-2-[(4-(methylsulphonyl)phenyl] ethanone of the formula

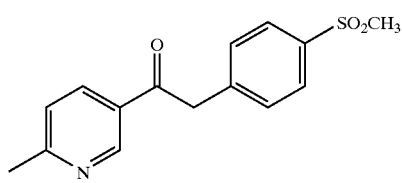

1-(6-methylpyridn-3-yl)-2-[(4-(methylsulphonyl)phenyl] ethanone is an important intermediate for preparing so-called COX-2 inhibitors, pharmaceutically active compounds having analgesic and antiinflammatory action (R. S. Friesen et al., Bioorganic & Medicinal Chemistry Letters 8 (1998)2777–2782; WO 98/0348).

The object of the invention was to provide a technically feasible process for preparing the intermediate of the formula I. This object was achieved by the novel process according to Claim 1.

The process according to the invention is characterized by five steps, where, in the first step a), 4-(methylthio)benzyl alcohol is converted with hydrochloric acid into 4-(methylthio)benzyl chloride, in the second step b), 4-(methylthio)benzyl chloride is converted with an alkali metal cyanide into 4-(methylthio)phenylacetonitrile, in the third step c), 4-(methylthio)phenylacetonitrile is condensed with a 6-methylnicotinic ester to give 3-[2-(4-(methylthio)phenyl)-2-cyanoacetyl](6-methyl) pyridine of the formula

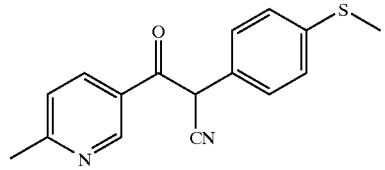

in the fourth step d), 3-[2-(4-(methylthio)phenyl)-2-cyanoacetyl](6-methyl)pyridine is hydrolysed and decarboxylated under acidic conditions to give 3-[2-(4-(methylthio)phenyl)acetyl](6-methyl)pyridine of the formula

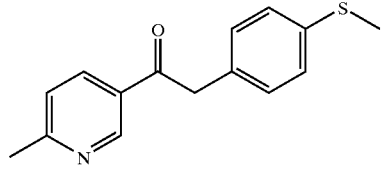

and, in the last step e), 3-[2-(4-(methylthio)phenyl)acetyl] (6-methyl)pyridine is oxidized to give the end product.

Step a

The chlorination of 4-(methylthio)benzyl alcohol to 4-(methylthio)benzyl chloride is carried out using hydrochloric acid, advantageously using concentrated hydrochloric acid, at a temperature of from 10° C. to 40° C.

The reaction is usually carried out in an organic solvent, advantageously in a water-immiscible solvent, such as, for example, in toluene.

Typically, the chlorination takes about 1 h to 4 h. The 4-(methylthio)benzyl chloride can be obtained in a simple manner by neutralizing the organic phase and removing the solvent. Further purification can be achieved by distillation.

Step b

The cyanidation of 4-(methylthio)benzyl chloride is carried out using an alkali metal cyanide, advantageously in the presence of a phase transfer catalyst. Suitable alkali metal cyanides are sodium cyanide or potassium cyanide. The phase transfer catalysts which can be chosen are known in the art. Suitable are tetraalkylammonium halides, such as, for example, tetra-n-butylammonium chloride or tetra-n-butylammonium bromide. In general, the reaction is carried out in the presence of a water-immiscible solvent, such as, for example, toluene; if appropriate, water can be added. The reaction temperature is advantageously from 60° C. to 100° C. After a reaction time of 1 h to 6 h, the product can be isolated in a simple manner from the organic phase by removing the solvent. Further purification of the product can be achieved by recrystallization from, for example, diisopropyl ether.

Step c

In the third step, (methylthio)phenyl)acetonitrile is condensed with a 6-methylnicotinic ester to give 3-[2-(4-methylthio)phenyl)-2-cyanoacetyl](6-methyl)pyridine of the formula

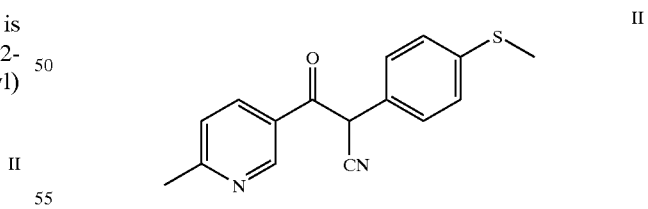

The condensation is advantageously carried out in the presence of an alkali metal alkoxide, at a temperature between 60° C. and 110° C. Suitable alkali metal alkoxides are, for example, sodium methoxide or potassium tert-butoxide. The reaction is advantageously carried out in the presence of a lower alcohol or an aromatic hydrocarbon as solvent. After the condensation, the 3-[2-(4-(methylthio) phenyl)-2-cyanoacetyl](6-methyl)pyridine can be obtained, for example, by adding the reaction mixture to cold water and precipitating the product from the aqueous phase by acidifying it slightly.

Step d
Hydrolysis and decarboxylation to give 3-[2-(4-(methylthio)phenyl)acetyl](6-methyl)pyridine of the formula

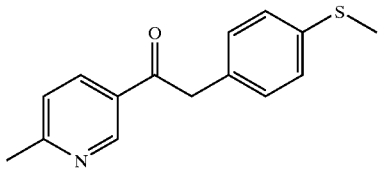

III are carried out under acidic conditions. Suitable acids are hydrochloric acid, phosphoric acid or mixtures of acetic acid with a mineral acid. Advantageously, a mixture of acetic acid and a mineral acid is employed, at a temperature of from 50° C. to 115° C. Particular preference is given to mixtures of acetic acid With concentrated hydrochloric aid or mixtures of acetic acid with concentrated sulphuric acid. If appropriate, a certain amount of water can be added to the mixtures. Good results were obtained using mixtures of acetic acid/concentrate hydrochloric acid 1:3 or acetic acid/concentrated sulphuric acid/water 1:1:1. After a reaction time of about 1 h to 20 h, the mixture can be neutralized using, for example, an aqueous ammonia solution, as a result of which the product precipitates out and can be isolated in a simple manner.

Step e
Oxidation of 3-[2-(4-(methylthio)phenyl)acetyl](6-methyl)pyridine to the end product is advantageously carried out using hydrogen peroxide in the presence of an alkali metal tungstate, at a temperature of from 10° C. to 40° C., preferably at about 20° C. A particularly suitable alkali metal tungstate is sodium tungstate of the formula $Na_4WO0.2H_4O$. The alkali metal tungstate is generally employed in catalytic amounts of from 0.5 mol % to 20 mol %, based on the 3-[2-(4-(methylthio)phenyl)acetyl](6-methyl)pyridine used. The reaction is advantageously carried out in the presence of a lower alcohol as solvent. After a reaction time of about 1 h to 6 h, the end product can be precipitated out by addition of water and then be isolated without any problems.

EXAMPLES

Preparation of 4-(methylthio)benzyl chloride

Under an atmosphere of nitrogen, 78.7 g (500 mmo)l [sic] of 4-(methylthio)benzyl alcohol were dissolved in 154.5 g of toluene. 131.6 g, (1.3 mol) of conc. HCl were added, and the mixture was stirred at 20–25° C. for 30 min. After 2 h (no starting material left according to TLC), the reaction mixture was diluted with 349 g of toluene and the aqueous phase was separated off. The organic phase was neutralized using 14.0 g of NaHCO and, after 15 min, filtered, and the solvent was evaporated. The residue that remained consisted of 107.4 a of a yellow oil with toluene, corresponding to a yield of >95% (according to NMR).

| $^1$H-NMR (CDCl$_3$): | 7.30 (2H, d); |
| --- | --- |
| | 7.22 (2H, d); |
| | 4.55 (2H, s); |
| | 2.47 (3H, s); |
| $^1$H-NMR (DMSO): | 7.37 (2H, d); |
| | 7.25 (2H, d); |
| | 4.73 (2H, d); |
| | 2.47 (3H, s). |

Preparation of 4-(methylthio)phenylacetonitrile

Under an atmosphere of nitrogen, 25.9 g (150 mmol) of 4-(methylthio)benzyl chloride were dissolved in 45.5 g of toluene. 9.29 g (180 mmol) of sodium cyanide, 0.92 g (2.9 mmol) of tetrabutylammonium chloride and 14.4 g of water were then added. The mixture was stirred at 80–85° C. for 2 h. The reaction mixture was admixed with 30 g of toluene and 45 g of water, the aqueous phase was decanted off and the organic phase was concentrated. This gave a residue of 24.6 g of the title product in a yield of >95% (according to NMR) in the form of a pink solid.

| $^1$H-NMR (CDCl$_3$): | 7.25 (4H, m); |
| --- | --- |
| | 3.70 (2H, s); |
| | 2.47 (3H, s). |

Preparation of 3-[2-(4-(methylthio)phenyl)-2-cyanoacetyl](6-methyl)pyridine

Under an atmosphere of nitrogen, a mixture of 38.5 g (250 mmol) of ethyl 6-methylnicotinate, 29.9 g (500 mmol) of sodium methoxide (90.5%) and 300 ml of toluene was added, at 85–90° C. and over the course of 30 min, to a solution of 47.3 g (250 mmol) of 4-(methylthio) phenylacetonitrile in 75 ml of toluene. This mixture was stirred under reflux for 14 h, then distilled until the overhead temperature exceeded 110° C. and kept at reflux for another 6 h. The reaction mixture was poured into 500 g of ice water, the organic phase was decanted off and the aqueous phase was extracted with 3×100 ml of toluene. The aqueous phase was acidified to pH 6.0 using conc. HCl. The resulting yellow-beige suspension was filtered and the residue was washed with water and dried. This gave 53.9 g (76%) of the title product in the form of a yellow solid.

| $^1$H-NMR (CDCl$_3$): | 9.00 (1H, s); |
| --- | --- |
| | 8.10 (1H, d); |
| | 7.3 (5H, m); |
| | 5.45 (1H, s); |
| | 2.60 (3H, s); |
| | 2.45 (3H, s). |

Preparation of 3-[2-(4-(methylthio)phenyl)acetyl](6-methyl)pyridine

A mixture of 8.0 g (28 mmol) of 3-[2-(4-(methylthio)phenyl)-2-cyanoacetyl](6-methyl)pyridine, 20 ml of acetic acid and 60 ml of concentrated hydrochloric acid was heated at 95° C. to 100° C. for 1.5 h. The orange solution was cooled and adjusted to pH 10 using concentrated ammonia solution. The resulting yellow-beige suspension was filtered and the residue was washed with water and dried. This gave 5.35 g (74.3) of the title product in the form of a yellow solid.

| $^1$H-NMR (CDCl$_3$): | 9.10 (1H, s); |
| --- | --- |
| | 8.15 (1H, d); |
| | 7.2 (5H, m); |
| | 4.21 (2H, s); |
| | 2.61 (3H, s); |
| | 2.45 (3H, s). |

Preparation of 1-(6-methylpyridin-3-yl)-2-[(4-(methylsulphonyl)phenyl]ethanone

Under an atmosphere of nitrogen, a suspension of 8.9 g (34.5 mmol) of 3-[2-(4-(methylthio)phenyl)acetyl](6- methyl)pyridine in 90 ml of methanol was heated to 55° C. and adjusted to pH 4.5 using 2 N sulphuric acid. An aqueous solution of 0.22 2 N (0.7 mmol) of sodium tungstate in 7 ml of water was then added. At 55° C., 10 mol of hydrogen peroxide were then added over the course of 1 h, and the mixture was then cooled to room temperature and filtered. The slightly beige filtration residue was washed using 2×30 ml of a mixture of water/isopropanol 2:1 and 2×30 ml of water and then dried under reduced pressure at room temperature. This gave 7.43 g of the title product in a yield of 75%.

| $^1$H-NMR (CDCl$_3$): | 9.15 (1H, s); |
| | 8.18 (1H, d); |
| | 7.92 (2H, d); |
| | 7.47 (2H, d); |
| | 7.30 (1H, d); |
| | 4.39 (2H, s); |
| | 3.04 (3H, s); |
| | 2.63 (3H, s). |

What is claimed is:

1. A process for preparing 1-(6-methylpyridin-3-yl)-2-[4-(methylsulfonyl)phenyl]ethanone of the formula I:

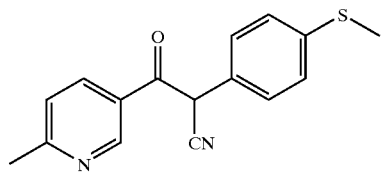

comprising:

in a first step, condensing 4-(methylthio)phenylacetonitrile with a 6-methylnicotinic ester to give 3-[2-(4-(methlthio)phenyl)-2-cyanoacetyl](6-methyl)pyridine of the formula II:

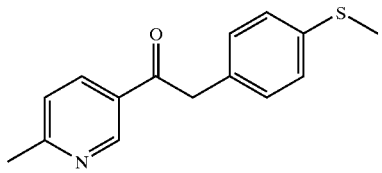

in a second step, hydrolyzing and decarboxylating the compound of formula II under aidic conditions using a mixture of acetic acid and a mineral acid, to give 3-[2-(4-(methylthio)phenyl)acetyl](6-methyl)pyridine of the formula III:

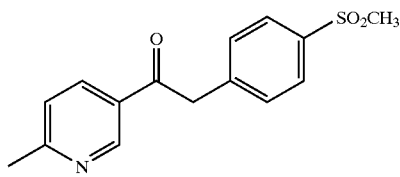

and, finally, in a last step, oxidizing said compound of formula III to give the end product.

2. The process according to claim 1, wherein said mixture in the second step is used at a temperature of from 50 to 115° C.

* * * * *